US011033598B2

(12) United States Patent
Cho et al.

(10) Patent No.: US 11,033,598 B2
(45) Date of Patent: Jun. 15, 2021

(54) PHARMACEUTICAL COMPOSITION FOR PREVENTING OR TREATING HEARING LOSS COMPRISING OAT EXTRACT AS AN ACTIVE INGREDIENT

(71) Applicants: INDUSTRY FOUNDATION OF CHONNAM NATIONAL UNIVERSITY, Gwangju (KR); CHONNAM NATIONAL UNIVERSITY HOSPITAL, Gwangju (KR); REPUBLIC OF KOREA(MANAGEMENT : RURAL DEVELOPMENT ADMINISTRATION), Jeollabuk-do (KR)

(72) Inventors: Hyong Ho Cho, Gwangju (KR); Hyung Seok Kim, Gwangju (KR); Sung Su Lee, Gwangju (KR); Yu Young Lee, Gyeonggi-do (KR)

(73) Assignees: INDUSTRY FOUNDATION OF CHONNAM NATIONAL UNIVERSITY, Gwanju (KR); CHONNAM NATIONAL UNIVERSITY HOSPITAL, Gwangju (KR); REPUBLIC OF KOREA (MANAGEMENT : RURAL DEVELOPMENT ADMINISTRATION), Jeollabuk-Do (KR)

( * ) Notice: Subject to any disclaimer, the term of this patent is extended or adjusted under 35 U.S.C. 154(b) by 207 days.

(21) Appl. No.: 16/133,033

(22) Filed: Sep. 17, 2018

(65) Prior Publication Data
US 2019/0076499 A1  Mar. 14, 2019

Related U.S. Application Data

(63) Continuation of application No. PCT/KR2016/014294, filed on Dec. 7, 2016.

(30) Foreign Application Priority Data

Mar. 16, 2016 (KR) .................. 10-2016-0031516
Sep. 22, 2016 (KR) .................. 10-2016-0121291

(51) Int. Cl.
*A61K 36/899* (2006.01)
*A61K 36/00* (2006.01)
*A61K 45/06* (2006.01)
*A61K 31/167* (2006.01)
*A61K 31/196* (2006.01)
*A61P 27/16* (2006.01)

(52) U.S. Cl.
CPC .......... *A61K 36/899* (2013.01); *A61K 31/167* (2013.01); *A61K 31/196* (2013.01); *A61K 45/06* (2013.01); *A61P 27/16* (2018.01)

(58) Field of Classification Search
None
See application file for complete search history.

(56) References Cited

U.S. PATENT DOCUMENTS

| 8,758,836 | B2 | 6/2014 | Yoshpe et al. | |
|---|---|---|---|---|
| 2001/0044099 | A1* | 11/2001 | Rappaport | G16H 10/20 434/323 |
| 2006/0100274 | A1* | 5/2006 | Meydani | A61K 31/195 514/534 |
| 2009/0306225 | A1 | 12/2009 | Lichter et al. | |
| 2011/0092500 | A1* | 4/2011 | Sandner | A61P 43/00 514/234.2 |
| 2014/0249160 | A1 | 9/2014 | Miller | |
| 2017/0340586 | A1* | 11/2017 | Hosoya | A61P 27/16 |

FOREIGN PATENT DOCUMENTS

KR    10-2013-0111038 A    10/2013

OTHER PUBLICATIONS

International Search Report for PCT/KR2016/014294 dated Mar. 13, 2017.
Sur, R. et al., "Avenanthramides, Polyphenols from Oats, Exhibit Anti-inflammatory and Anti-itch Activity", Archives of Dermatological Research, vol. 300, No. 10, pp. 569-574, 2008.
Bratt,K. et al., "Avenanthramides in Oats (*Avena sativa* L.) and Structure-antioxidant Activity Relationships", Journal of Agricultural and Food Chemistry, vol. 51, No. 3, pp. 594-600, 2003 (Abstract is submitted herewith).
Guo, W. et al., "Avenanthramides Inhibit Proliferation of human Colon Cancer Cell Lines in Vitro", Nutrition and Cancer, vol. 62, No. 8, pp. 1007-1016, 2010.
Yang. J. et al., "In Vitro Total Antioxidant Capacity and Anti-inflammatory Activity of Three Common Oat-derived Avenanthramides", Food Chemistry, vol. 160, pp. 338-345, 2014.
European Search Report for EP16894694.5 dated Oct. 30, 2019 from European patent office in a counterpart European patent application.

* cited by examiner

*Primary Examiner* — Michael Barker
*Assistant Examiner* — Randall O Winston
(74) *Attorney, Agent, or Firm* — The PL Law Group, PLLC

(57) ABSTRACT

A method for preventing or treating hearing loss includes administering a composition comprising an oat extract to a subject. The method may use avenanthramide or a derivative thereof an oat extract. The oat extract has an effect on hair cells of the cochlea, spinal ganglion cells, and angiocytes, and an effect of inhibiting occurrence of hearing loss and can be usefully used for preventing or treating hearing loss. In particular, since the oat extract is a natural product and has stability without cytotoxicity, the composition containing the oat extract as an active ingredient has a safety advantage for long-term use without side effects on the human body.

8 Claims, 10 Drawing Sheets

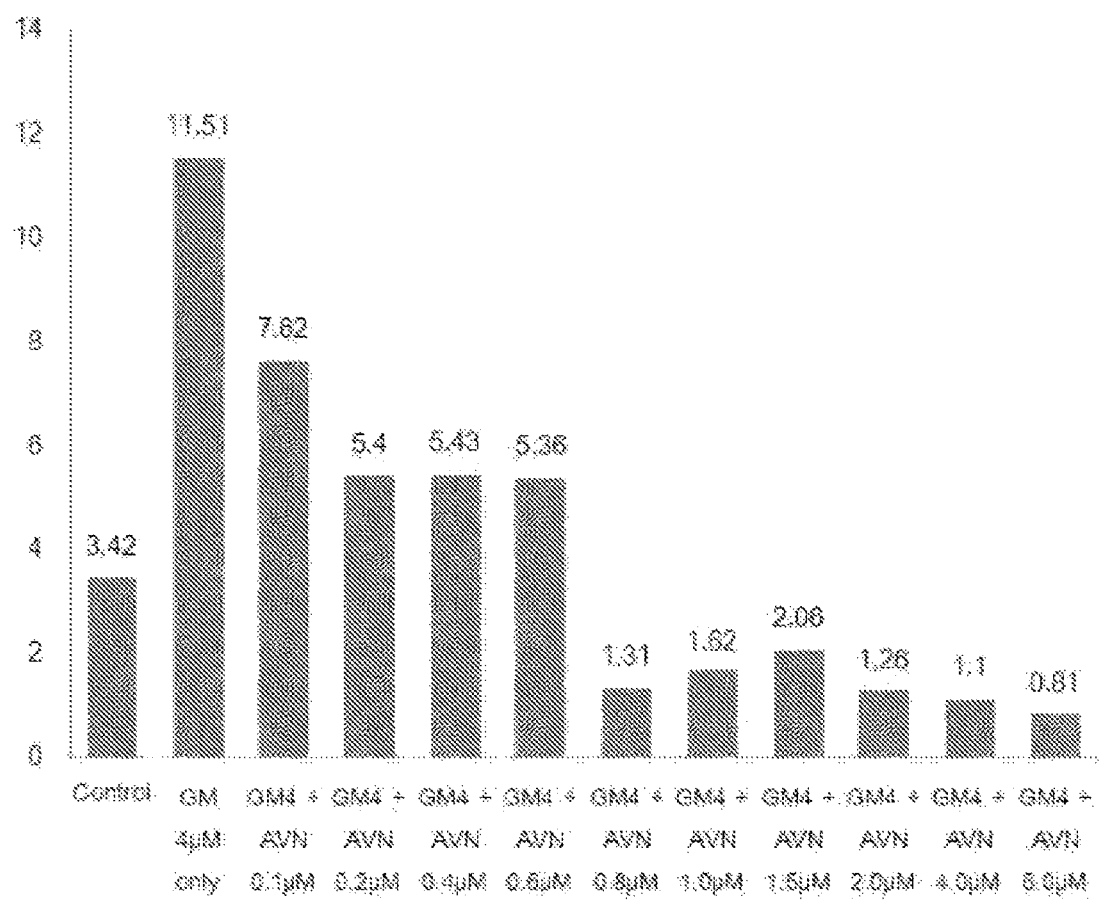

FIG. 5A
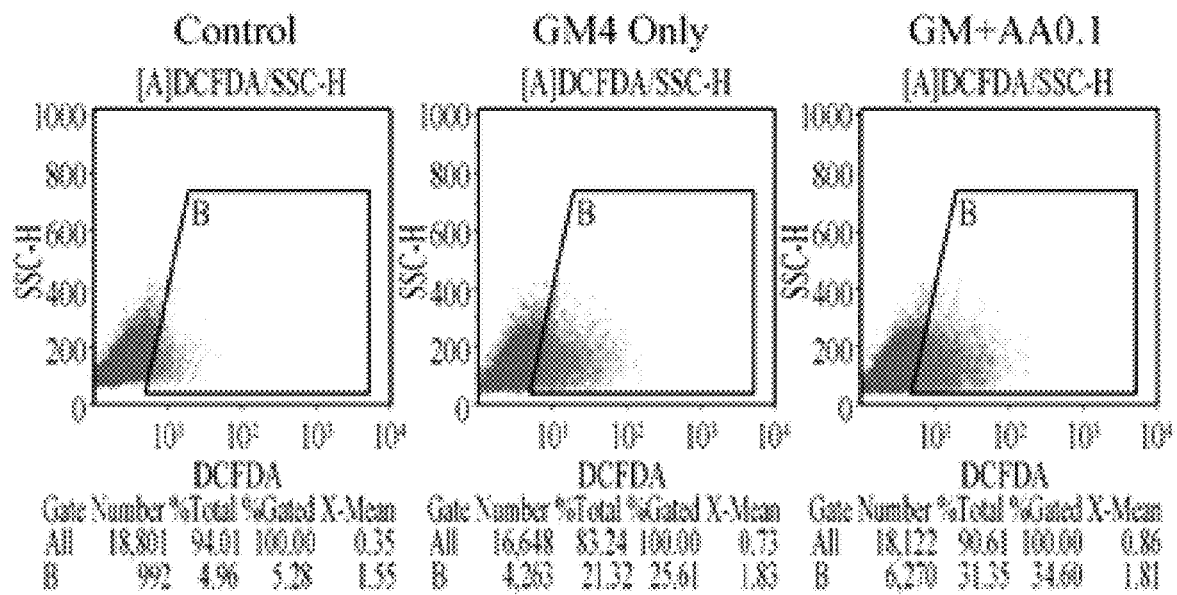
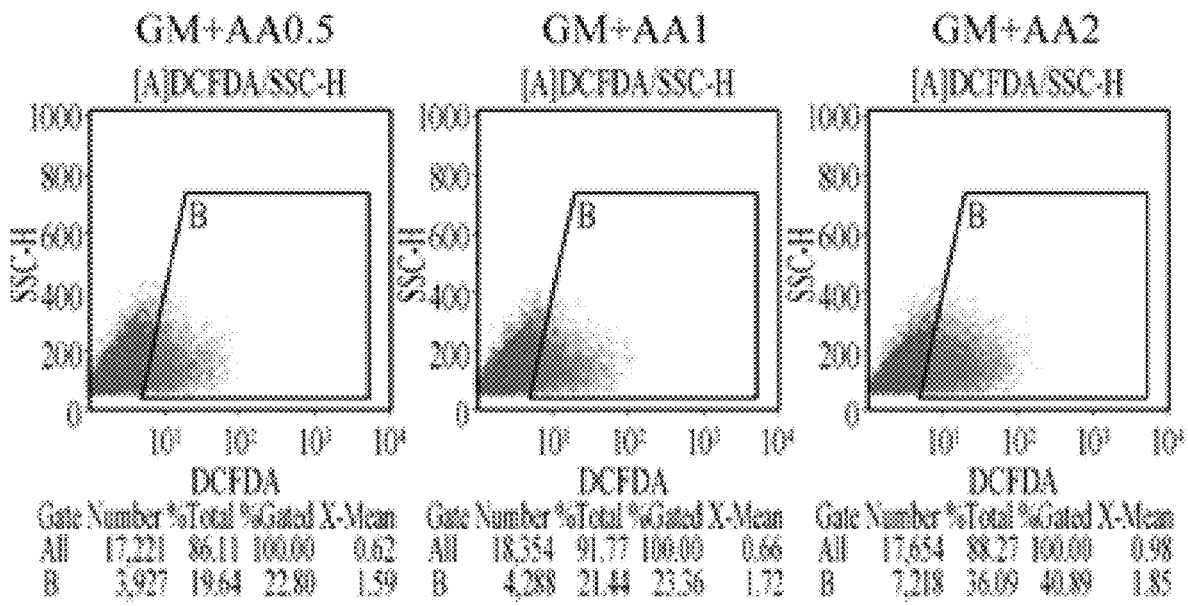

FIG. 7
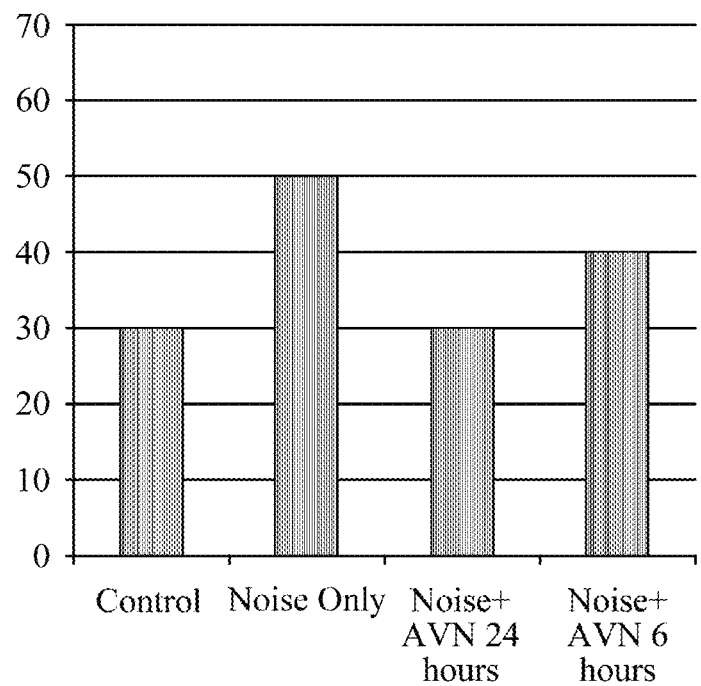
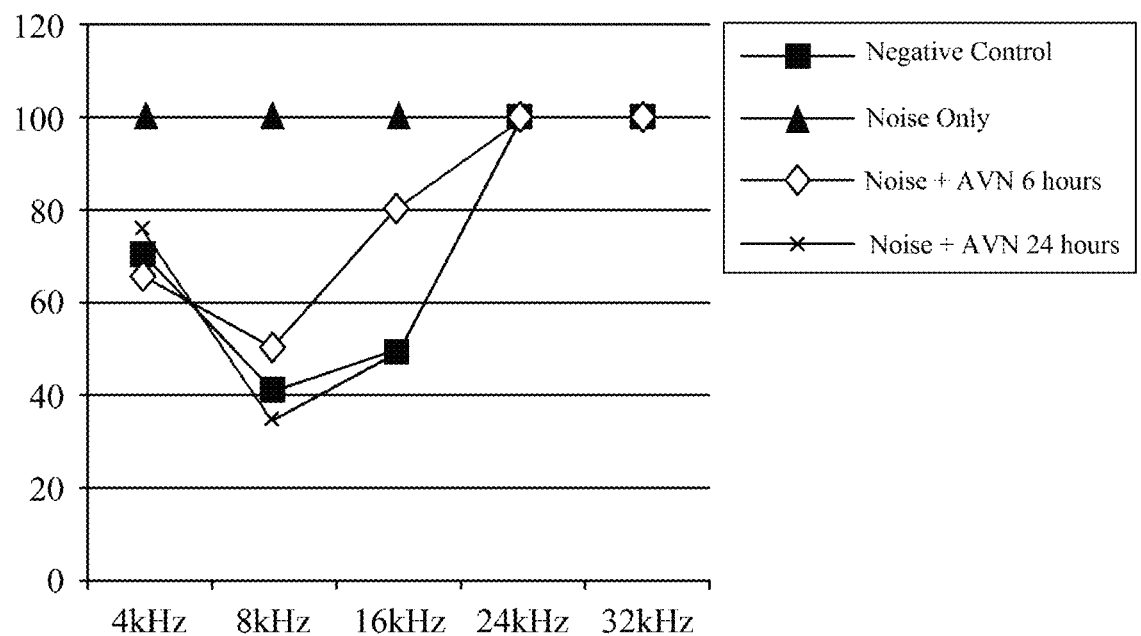

FIG. 8
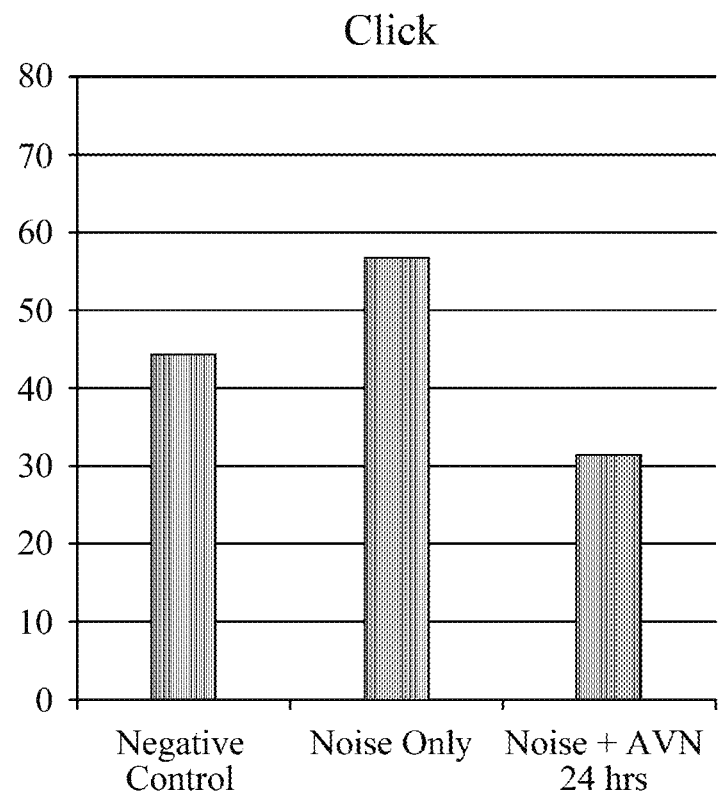
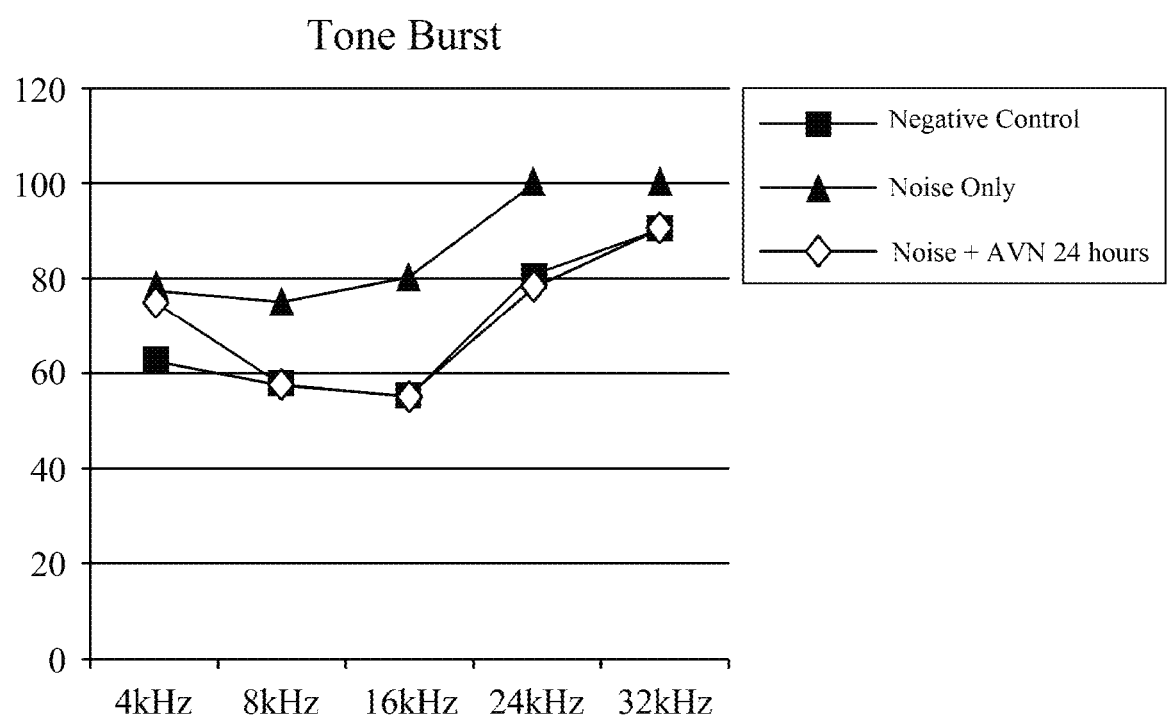

FIG. 9
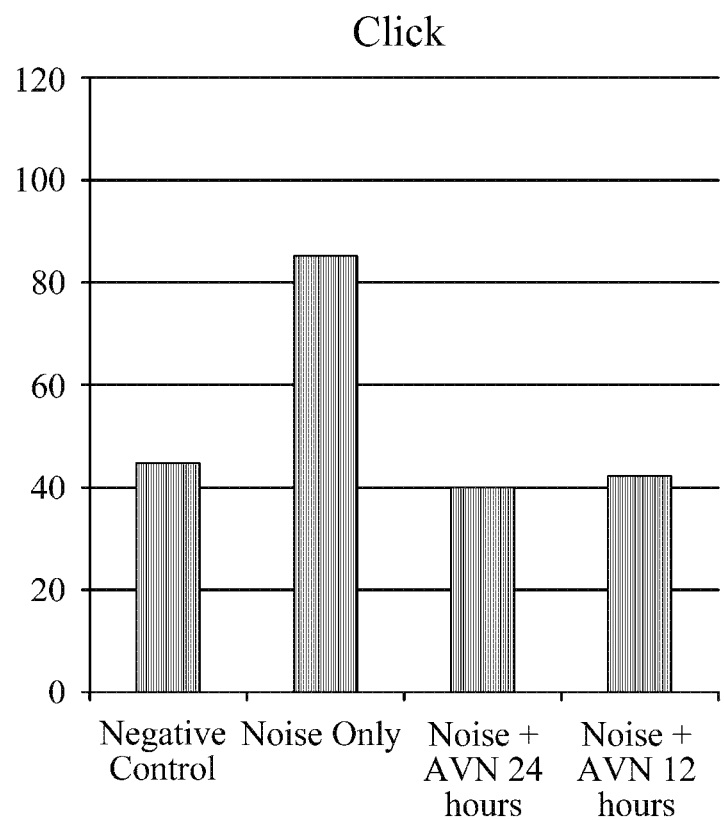
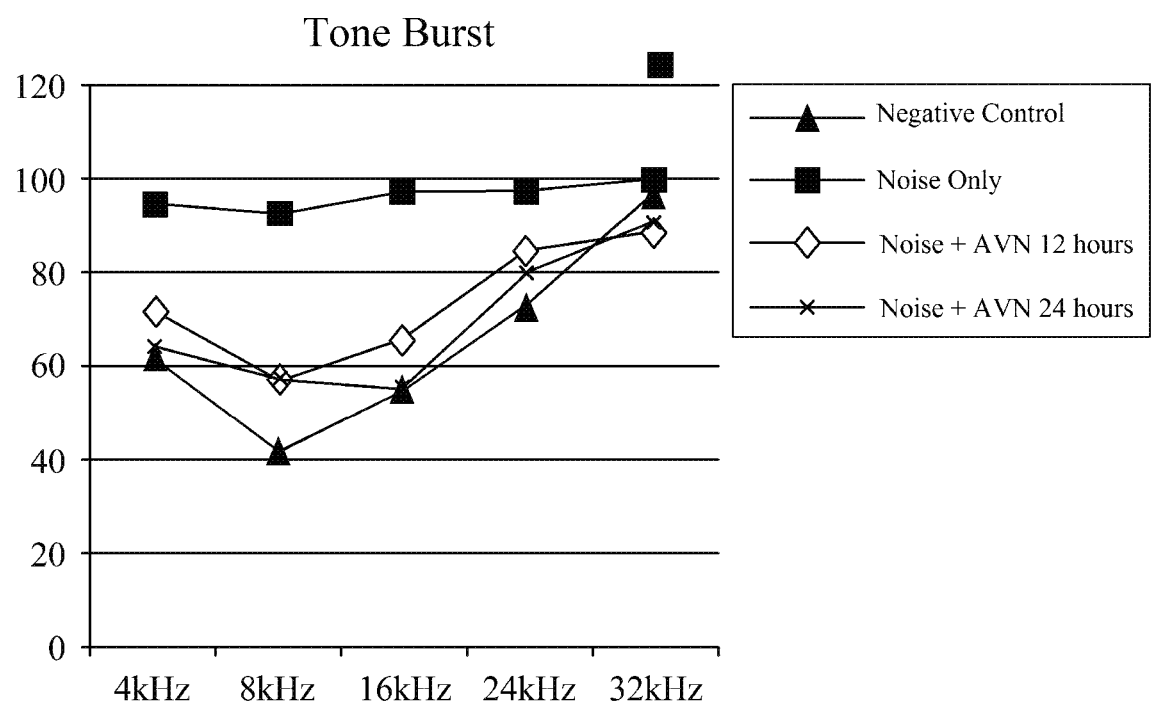

ND OAT EXTRACT AS AN
ACTIVE INGREDIENT

PHARMACEUTICAL COMPOSITION FOR PREVENTING OR TREATING HEARING LOSS COMPRISING OAT EXTRACT AS AN ACTIVE INGREDIENT

CROSS REFERENCE TO RELATED APPLICATIONS AND CLAIM OF PRIORITY

The present application is a continuation application to International Application No. PCT/KR2016/014294, filed Dec. 7, 2016, which claims priority to the benefit of Korean Patent Application No. 10-2016-0031516 filed on Mar. 16, 2016 and 10-2016-0121291 filed on Sep. 22, 2016 in the Korean Intellectual Property Office, the disclosures of which are incorporated by reference herein in their entirety.

BACKGROUND

1. Field of the Invention

The present invention relates to a pharmaceutical composition for preventing or treating hearing loss comprising an oat extract as an active ingredient, and more specifically, to a pharmaceutical composition for preventing or treating hearing loss comprising, as an active ingredient, an oat extract, for example, avenanthramide or a derivative thereof.

2. Discussion of the Related Art

Hearing loss refers to a condition in which hearing is abnormal by various causes and the hearing is deteriorated or lost. The ear consists of the outer ear (from the auricle to the eardrum), the middle ear (from the eardrum to the entrance of the cochlea), and the inner ear (inside the cochlea), and if a problem occurs at any place thereof, the hearing loss is caused. The hearing loss is classified into hearing loss (conductive hearing loss) due to disorders of the outer ear and the middle ear and hearing loss (sensorineural hearing loss) due to disorders of the inner ear and the auditory nerves. The hearing loss due to disorders of the outer ear and the middle ear is restored if the disorders are treated, but the hearing loss due to disorders of the inner ear and the auditory nerves is not restored in many cases even if the disorders are treated to cause great inconvenience to the patients.

The hearing loss due to disorders of the inner ear and the auditory nerves may be classified into senile hearing loss, childhood hearing loss, Meniere's disease, sudden hearing loss, noise-induced hearing loss, ototoxic hearing loss, and the like, and among them, the noise-induced hearing loss and the ototoxic hearing loss due to noise and drugs are most common.

The noise-induced hearing loss (acoustic trauma) is very similar to the ototoxic hearing loss in the form of hearing loss or wow lesion. The noise-induced hearing loss is caused by receiving oxidative stress in the auditory cells when the ear is exposed to strong noise to generate reactive oxygen species (ROS) and inducing apoptosis by the generated ROS. Since the extent of cell damage after exposure to strong noise is dependent on the antioxidant status of the cells, the degree of damage may be reduced by increasing and maintaining the antioxidant status. However, so far, no drugs for preventing or treating the noise-induced hearing loss have been developed.

The ototoxic hearing loss is a side effect caused by using ototoxic drugs, and it is known that aminoglycoside antibiotics and some anticancer drugs cause the ototoxicity. The aminoglycoside antibiotics include streptomycin, kanamycin, gentamicin, neomycin, amikacin, tobramycin, netilmicin, dibekacin, sisomycin, livodomycin, and the like. The aminoglycoside antibiotics are mainly used for gram-negative bacterial infections, tuberculosis, deep-seated infections, and the like which do not properly react with general antibiotics. The aminoglycoside antibiotics exhibit ototoxic side effects during long-term administration or during short-term administration in some cases. The aminoglycoside antibiotics inhibit synthesis of proteins by binding to bacteria 30s ribosomal subunits to have antibacterial activity, and when the aminoglycoside antibiotics are continuously exposed to cochlear cells, apoptosis of outer hair cells and sensory hair cells of the corti organ occurs. It is known that the apoptosis is caused by the ROS in which a Ca++ complex is formed with the aminoglycoside antibiotics.

As described above, it is considered that the noise-induced hearing loss and the ototoxic hearing loss are caused by generating the ROS due to the noise and ototoxic drugs to cause the apoptosis. Accordingly, materials capable of effectively inhibiting generation of the ROS may become candidate materials exhibiting an effect of preventing or treating ototoxicity.

SUMMARY

Therefore, the present inventors made an effort to develop a pharmaceutical composition for preventing or treating hearing loss using natural substances and verified that an oat extract can effectively act in a gentamicin ototoxicity model, and as a result, completed the present invention.

The term "oat" used in the present specification is a plant which has been estimated to have spread from the eastern to the central Europe with barley around 5000 BC and used in Europe for 800 years or more for nutritional and medical purposes. The oat is a biennial edible crop as a monocotyledonous plant of Gramineae and referred to as *Avena sativa* L and includes about 70 species, but among them, only a few of species are cultured and mostly, a wild oat (*Avena sativa* L.) has been cultured. The oat has a height of about 90 cm, the leaf has a length of 15 to 30 cm, the width is 6 to 12 mm and flat, the sheath leaf is long, and the ligule is short and finely split. Flowers bloom from May to June and are panicles, and the branches turn and split again. The glume does not have a ridge, has many veins and spreads on both sides. The arista is wrapped inside and outside, hairy, and has a groove on one side. Fruits are made from oatmeal and eaten and are used as alcohol, raw materials of cookies and feedstuffs for livestock. It is known that an ingredient of the oat includes β-carotene, β-glucan, vitamin C, niacin, riboflavin, thiamine, retinol, dietary fiber, avenanthramide, and the like, and among them, the avenanthramide inhibits reactive oxygen species as an antioxidant. The avenanthramide may be classified into avenanthramide-A, avenanthramide-B, avenanthramide-C, avenanthramide-O, or avenanthramide-P.

In accordance with an embodiment of the present invention, the present invention provides a pharmaceutical composition for preventing or treating hearing loss comprising an oat extract as an active ingredient.

The oat extract may be avenanthramide or a derivative thereof. The avenanthramide may include, for example, avenanthramide-A, avenanthramide-B, avenanthramide-C, avenanthramide-O, or avenanthramide-P.

In the pharmaceutical composition for preventing or treating hearing loss according to the present invention, the oat extract may include 0.5 µM or more.

In the pharmaceutical composition for preventing or treating hearing loss according to the present invention, the hearing loss includes hearing loss due to noise ("noise-induced hearing loss") or hearing loss due to administration of ototoxic drugs ("ototoxic hearing loss"). For example, the ototoxic drug may include aminoglycoside antibiotics and anticancer agents, and preferably, the ototoxic drug may be at least one selected from a group consisting of streptomycin, kanamycin, gentamicin, neomycin, amikacin, tobramycin, netilmicin, dibekacin, sisomycin, livodomycin, cisplatin and carboplatin.

The embodiment of the present invention discloses an effect of the pharmaceutical composition of the present invention on ototoxic hearing loss caused by gentamicin which is a representative toxic drug. However, since the above-mentioned drugs induce apoptosis by a similar mechanism to gentamicin, that is, by generating reactive oxygen species (ROS) toxic hearing loss to cause ototoxic hearing loss, those skilled in the art will appreciate that the pharmaceutical composition of the present invention will have the same effect on ototoxic hearing loss due to ototoxic drugs other than gentamicin. In addition, since the noise-induced hearing loss has the same mechanism as that of the ototoxic hearing loss, those skilled in the art will appreciate that the pharmaceutical composition of the present invention will have the same effect on the noise-induced hearing loss.

In the pharmaceutical composition for preventing or treating hearing loss according to the present invention, the pharmaceutical composition may be formulated as a pharmaceutical agent suitable for transintestinal administration, that is, oral administration. The agent may be a form of tablets, foams, granules, or capsules. The pharmaceutical agent may be a single-administration formulation, and in this case, each administration formulation contains a predetermined amount of oat extract, for example, avenanthramide, and in addition, the pharmaceutical agent may be formulated by selecting and mixing suitable diluents, carriers, or other excipients according to a general pharmaceutical method. For example, the tablets may contain general granulating agents, diluents, binders, disintegrants, lubricants, stabilizers, colorants, shading agents, sweeteners and seasoning agents in addition to active fillers. In addition, other formulation techniques may be used, such as preparing tablets separated from the layer when stability is poor due to drug-drug interactions. In the pharmaceutical composition for preventing or treating hearing loss according to the present invention, the pharmaceutical composition may reduce generation of ROS by 20% or more.

In accordance with another embodiment of the present invention, the present invention provides an antibiotic composition with improved ototoxic hearing loss, comprising avenanthramide or a derivative thereof and an aminoglucoside antibiotic as an active ingredient.

In accordance with yet another embodiment of the present invention, the present invention provides an anticancer composition with improved ototoxic hearing loss, comprising avenanthramide or a derivative thereof and an aminoglucoside antibiotic as an active ingredient.

According to the present invention, avenanthramide as an oat extract has an effect on hair cells of the cochlea, spinal ganglion cells, and angiocytes, and an effect of inhibiting occurrence of hearing loss and can be usefully used for preventing or treating hearing loss. In particular, since the oat extract according to the present invention is a natural product and has stability without cytotoxicity, the composition of the present invention containing the oat extract as an active ingredient has a safety advantage for long-term use without side effects on the human body.

BRIEF DESCRIPTION OF THE DRAWINGS

FIG. 4 illustrates an increase rate of DCF fluorescent intensity in hearing loss model cells according to an avenanthramide-C treatment amount according to Examples 1 to 4;

FIGS. 5A and 5B illustrate an increase rate of DCF fluorescent intensity in hearing loss model cells according to an ascorbic acid treatment amount according to Comparative Example 1;

FIG. 7 illustrates an experimental result of measuring a hearing threshold in a hearing loss mouse model depending on treatment of avenanthramide according to Experimental Example 1;

FIG. 8 illustrates an experimental result of measuring a hearing threshold in a hearing loss mouse model depending on treatment of avenanthramide according to Experimental Example 1; and FIG. 9 illustrates an experimental result of measuring a hearing threshold in a hearing loss mouse model depending on treatment of avenanthramide according to Experimental Example 1.

DETAILED DESCRIPTION

Figure 1:
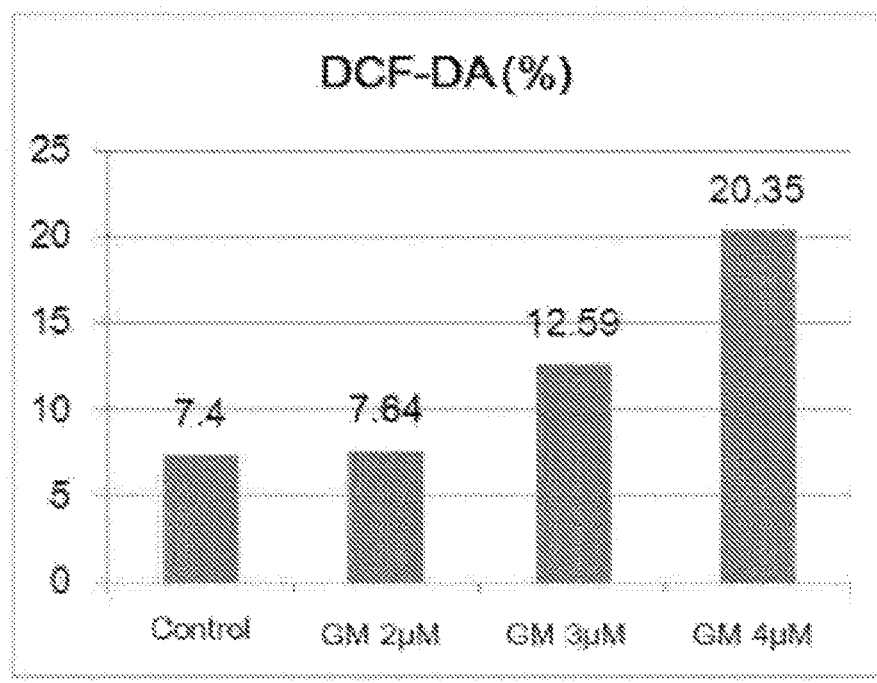
FIG. 1 illustrates an increase rate of DCF fluorescent intensity in hearing loss model cells due to gentamicin and avenanthramide according to Examples 1 and 2.

Hereinafter, embodiments of the present invention are described in detail with reference to the accompanying drawings. In describing the embodiments of the present invention, a detailed description of related known elements or functions will be omitted if it is deemed to make the gist of the present invention unnecessarily vague.

In this specification, when it is said that one element is 'connected' or 'coupled' with the other element, it may mean that the one element may be directly connected or coupled with the other element and a third element may be 'connected' or 'coupled' between the two elements. Furthermore, in this specification, when it is said that a specific element is 'included', it may mean that elements other than the specific element are not excluded and that additional elements may be included in the embodiments of the present invention or the scope of the technical spirit of the present invention.

Terms, such as the first and the second, may be used to describe various elements, but the elements are not restricted by the terms. The terms are used to only distinguish one element from the other element. For example, a first element may be named a second element without departing from the scope of the present invention. Likewise, a second element may be named a first element.

The present invention provides a pharmaceutical composition for preventing or treating hearing loss comprising an oat extract as an active ingredient.

The oat extract is avenanthramide or a derivative thereof. The avenanthramide may include, for example, avenanthramide-A, avenanthramide-B, avenanthramide-C, avenanthramide-O, or avenanthramide-P.

In the pharmaceutical composition for preventing or treating hearing loss according to the present invention, the oat extract may include 0.5 µM or more.

In the pharmaceutical composition for preventing or treating hearing loss according to the present invention, the hearing loss includes hearing loss due to noise ("noise-induced hearing loss") or hearing loss due to administration of ototoxic drugs ("ototoxic hearing loss").

The present invention provides an antibiotic composition with improved ototoxic hearing loss, comprising avenanthramide or a derivative thereof and an aminoglucoside antibiotic as an active ingredient.

The present invention provides an anticancer composition with improved ototoxic hearing loss, comprising avenanthramide or a derivative thereof and an ototoxic antibiotic as an active ingredient.

Hereinafter, the present invention will be described in detail by the following Examples. However, the following Examples just exemplify the present invention, and the contents of the present invention are not limited to the following Examples.

EXAMPLES

Example 1

Effect of Avenanthramide on Hearing Loss Model In Vitro 1-1. Culture of Hearing Loss Model Cell Line In order to determine an effect of an oat extract according to the present invention on hearing loss caused by active oxygen species, a DCF-DA assay was performed. A generation source of the active oxygen species used gentamicin as an aminoglucoside antibiotic which has been known to cause side effects that cause the loss of hair cells by forming ROS exceeding antioxidant defense capacity of inner ear cells. A HEI-OC1 cell line (House Ear Institute) which was known for an experiment of the inner ear cell included a 10% fetal bovine serum and 25 U/mL interferon-gamma, but had no antibiotic and was cultured in a Dulbecco's Modified Eagle medium (DMEM) containing glucose at a high concentration (25 mM). In this experiment, the HEI-OC1 cells were always cultured and differentiated under a non-permissive condition of 37° C. and 5% $CO_2$ and the experiment was performed with active metabolism.

1-2. Change in Hearing Loss Model Cells According to Gentamicin and Avenanthramide In order to verify whether the hearing loss model cells were influenced by treatment of gentamicin and avenanthramide, the generation of ROS was observed. The cells were seeded at $4 \times 10^5$ cells/well in a 6-well plate, treated with 0 µM, 0.5 µM, and 1 µM of avenanthramide-C, respectively, and cultured for 24 hrs under the condition of 37° C. and 5% $CO_2$, and then mixed and treated with 0 µM, 2 µM, 3 µM and 4 µM of gentamicin, respectively, as shown in Table 1, and cultured for 24 hrs under the condition of 37° C. and 5% $CO_2$. In the treated experiment model, in order to observe the generation of the ROS, a 6-carboxy-2',7'-dichlorodihydrofluorescein diacetate (DCF-DA) test which was a testing method commonly used in the art was applied. As described above, after treatment with avenanthramide and gentamicin and culture, the medium was removed, and 10 µM 6-carboxy-2',7'-dichlorodihydrofluorescein diacetate (DCF-DA, Sigma) was added and cultured for 30 minutes. After the cells were washed with a PBS buffer two times, the cells were isolated from the culture dish with 0.05% Trypsin/EDTA. Thereafter, the cells passed through a 40 µm filter paper to be homogenized, and then subjected to fluorescence analysis using a flow cytometry (FACSCalibur™, BD bioscience) (excitation: 488 nm; output: 519 nm). The increase rate of the DCF fluorescence intensity was measured, and the results were illustrated in Table 1 and FIG. 1.

TABLE 1

| | |
|---|---|
| Negative Control | 0% |
| Gentamicin: 0 µM | 7.4% |
| Gentamicin: 2 µM | 7.64% |
| Gentamicin: 3 µM | 12.59% |
| Gentamicin: 4 µM | 20.35% |

Figure 2:
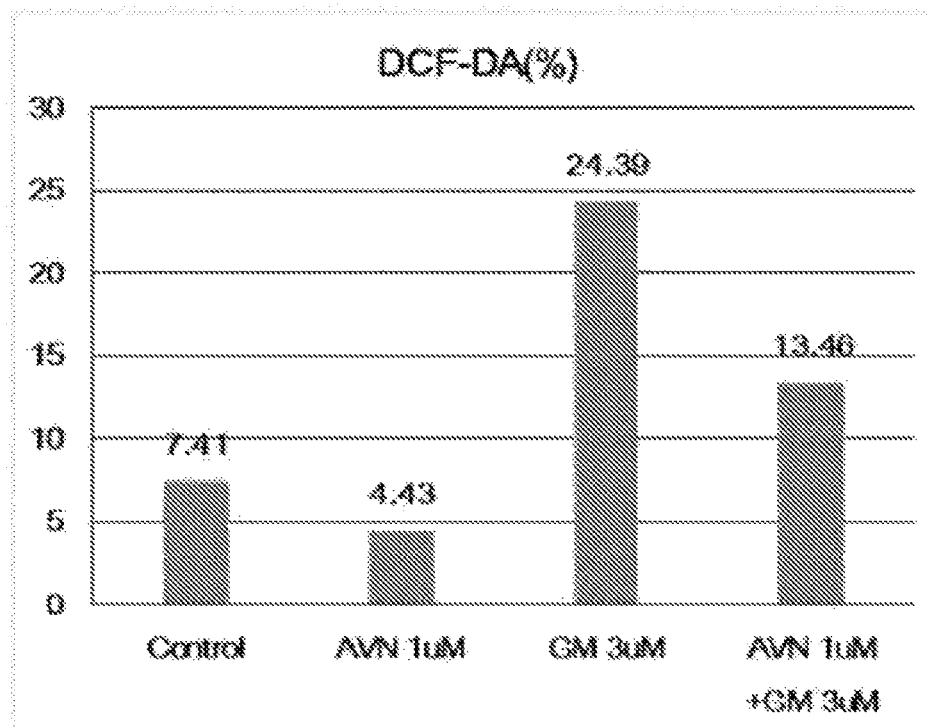
FIG. 2 illustrates a ROS generation rate in hearing loss model cells due to gentamicin and avenanthramide according to Examples 1 and 2.

As illustrated in Table 1, it was confirmed that as the treatment amount of gentamicin was increased, the generation amount of the ROS was increased to effectively cause the toxicity in the HEI-OC1 cell line (see FIG. 1). When the gentamicin of 10 µM or more was treated, the cells were almost died and a concentration of 10 µM or less was used for the experiment. In addition, when avenanthramide was pretreated for 24 hours under the same conditions, it was shown that the amount of ROS generated by gentamicin decreased. Thus, it was confirmed that avenanthramide was used for the treatment and prevention of hearing loss caused by the ROS may be used effectively (see Table 2 and FIG. 2).

TABLE 2

| Control | AVN 1 µM | GM 3 µM | AVN 1 µM + GM 3 µM |
|---|---|---|---|
| 7.41 | 4.43 | 24.39 | 13.46 |

1-3. Change in Hearing Loss Model Cells According to Avenanthramide-C Treatment Time The cells were seeded at $4 \times 10^5$ cells/well in a 6-well plate, treated with 0 µM and 0.5 µM of avenanthramide-C, respectively, and cultured for 24 hrs under the condition of 37° C. and 5% $CO_2$, and then mixed and treated with 0 µM and 3 µM of gentamicin, respectively, as shown in Table 3, and cultured for 3, 12, and 24 hrs under the condition of 37° C. and 5% $CO_2$, respectively. After the culture, like Examples 1 and 2, the DCF-DA test was performed and the results were illustrated in Table 3 and FIG. 3 below.

TABLE 3

| Control | GM 3 µM | AVN only | AVN 3 hr + GM 3 µM | AVN 12 hr + GM 3 µm | AVN 24 hr + GM 3 µM |
|---|---|---|---|---|---|
| 33.27 | 56.06 | 32.27 | 45.85 | 45.12 | 34.89 |

Figure 3:
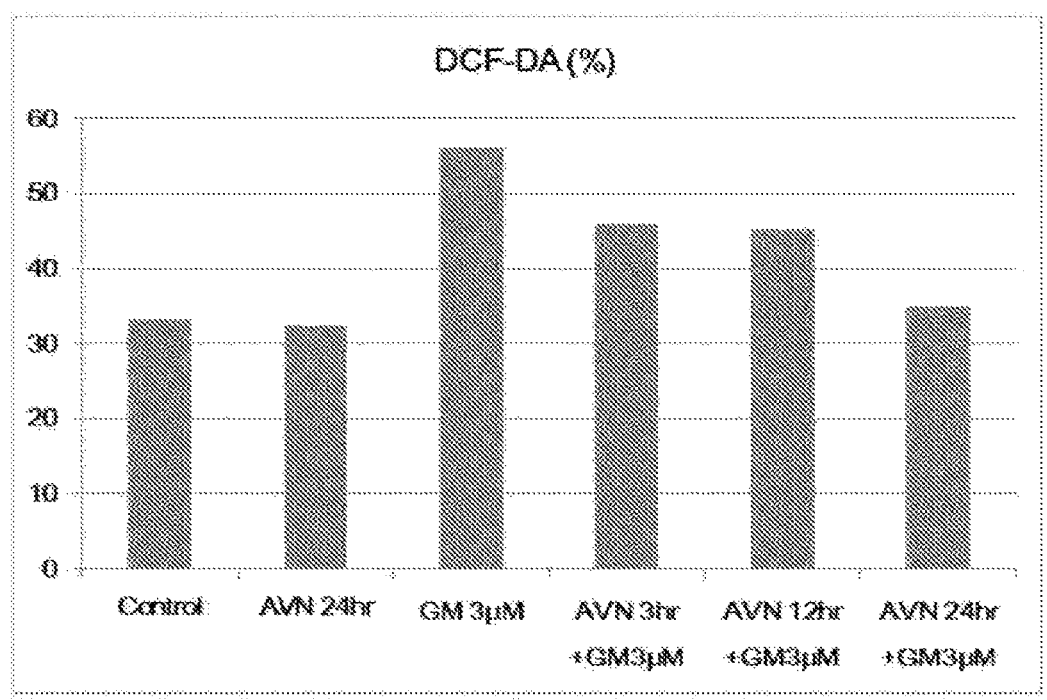
FIG. 3 illustrates an increase rate of DCF fluorescent intensity in hearing loss model cells according to an avenanthramide-C treatment time according to Examples 1 to 3.

As seen from Table 3, it was verified that as the avenanthramide treatment time increased, the ROS generated by gentamicin decreased, and particularly, as the treatment time of avenanthramide was 24 hours or more, an effect of suppressing hearing loss caused by the ROS was exhibited up to the same level as a control (see FIG. 3). The treatment of avenanthramide for 24 hours or more had no particular benefit in reducing the ROS generated by gentamicin.1-4.

Change in hearing loss model cells according to avenanthramide-C treatment amount The cells were seeded at 4×10$^5$ cells/well in a 6-well plate, treated with 0 μM to 6.0 μM of avenanthramide-C, respectively, and cultured for 24 hrs under the condition of 37° C. and 5% $CO_2$, and then mixed and treated with 0 μM or 4 μM of gentamicin as shown in Table 4, and cultured for 24 hrs under the condition of 37° C. and 5% $CO_2$. After the culture, like Example 1-1, the DCF-DA test was performed and the results were illustrated in Table 4 and FIG. 4 below.

TABLE 4

| Control | 3.42 |
|---|---|
| GM 4 μM only | 11.51 |
| GM 4 μM + AVN 0.1 μM | 7.62 |
| GM 4 μM + AVN 0.2 μM | 5.4 |
| GM 4 μM + AVN 0.4 μM | 5.43 |
| GM 4 μM + AVN 0.6 μM | 5.36 |
| GM 4 μM + AVN 0.8 μM | 1.31 |
| GM 4 μM + AVN 1.0 μM | 1.62 |
| GM 4 μM + AVN 1.5 μM | 2.06 |
| GM 4 μM + AVN 2.0 μM | 1.26 |
| GM 4 μM + AVN 4.0 μM | 1.1 |
| GM 4 μM + AVN 6.0 μM | 0.81 |

As seen from Table 4, it was verified that when the amount of avenanthramide was 0.1 μM, the avenanthramide did not affect the damage by gentamicin, but when the amount of avenanthramide was 0.2 μM, the amount of ROS was decreased by 50% or more as compared to the case where avenanthramide was not supplied in the occurrence of the hearing loss caused by the ROS (see FIG. 4).

Comparative Example 1

Effect of Ascorbic Acid on Hearing Loss Model Cells In Vitro

Before 24 hours for administering gentamicin (4 μM) in a HEI-OC1 cell line using the same method as the Example, ascorbic acid was treated with an amount of 0.1 μg/ml to 2 μg/ml and after 24 hours of gentamicin treatment, the DCF-DA test according to the content of ascorbic acid was performed. The result was illustrated in FIGS. 5A and 5B.

Figure 5B:
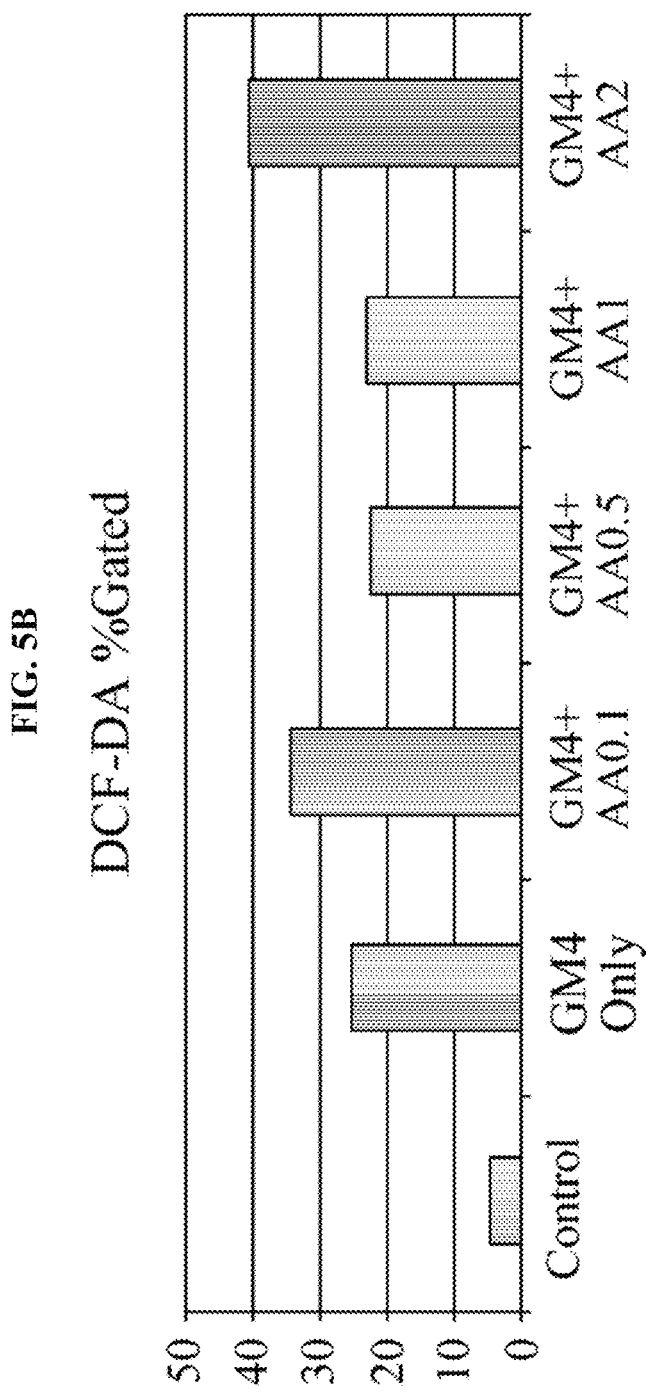

As seen from FIGS. 5A and 5B, it was not verified that when the ascorbic acid was administered, particular protection of hearing loss was shown as compared to the case where only the gentamicin was administered.

Comparative Example 2

Effect of β-glucan on Hearing Loss Model Cells In Vitro

Before 24 hours for administering gentamicin (4 μM) in a HEI-OC1 cell line using the same method as the Example, β-glucan was treated with an amount of 0.1 μg/ml to 2 μg/ml and after 24 hours of gentamicin treatment, the DCF-DA test according to the content of β-glucan was performed. The result was illustrated in FIGS. 6A and 6B.

Figure 6A:
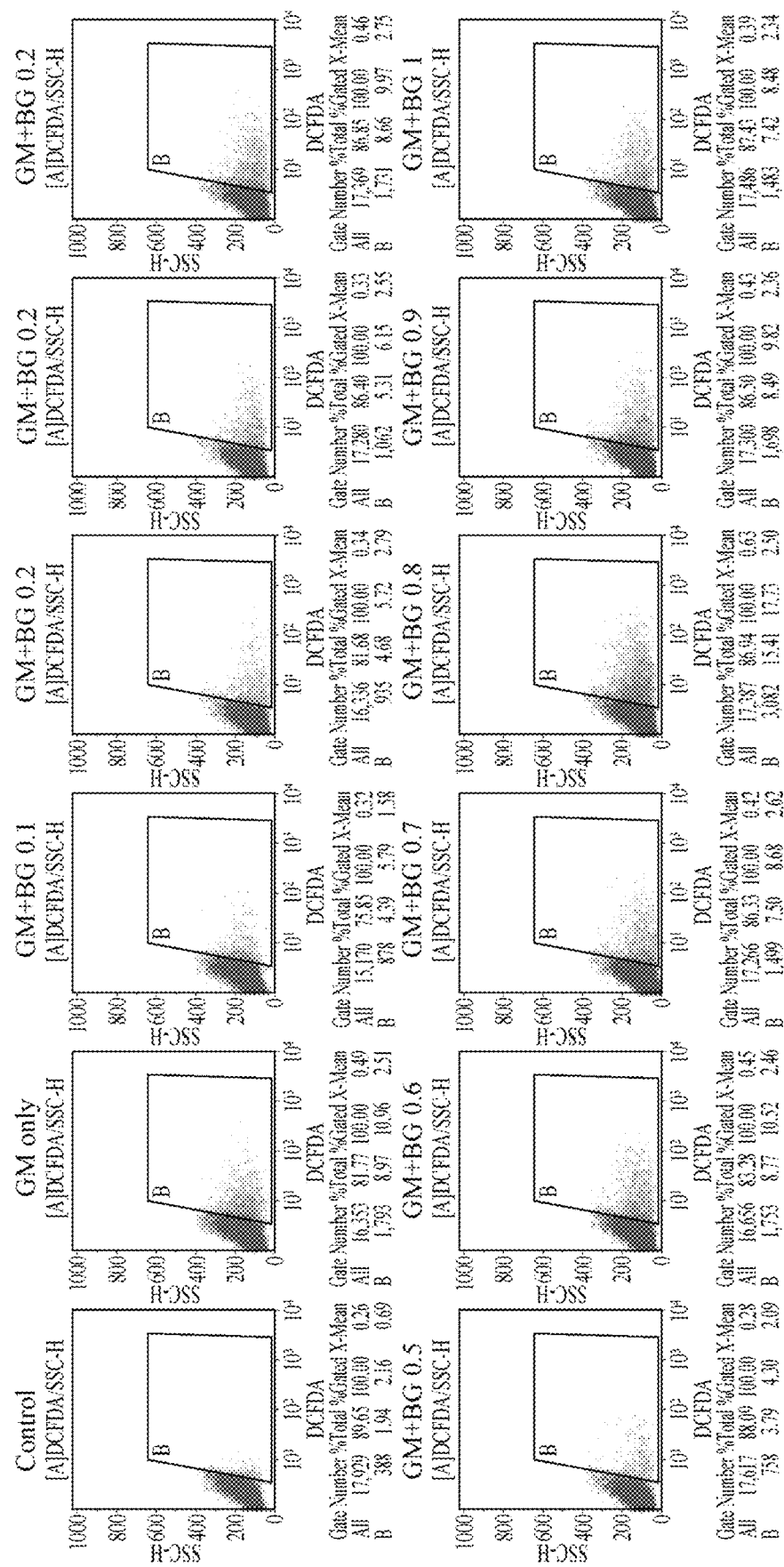
FIGS. 6A and 6B illustrate an increase rate of DCF fluorescent intensity in hearing loss model cells according to a β-glucan treatment amount according to Comparative Example 1.
Figure 6B:
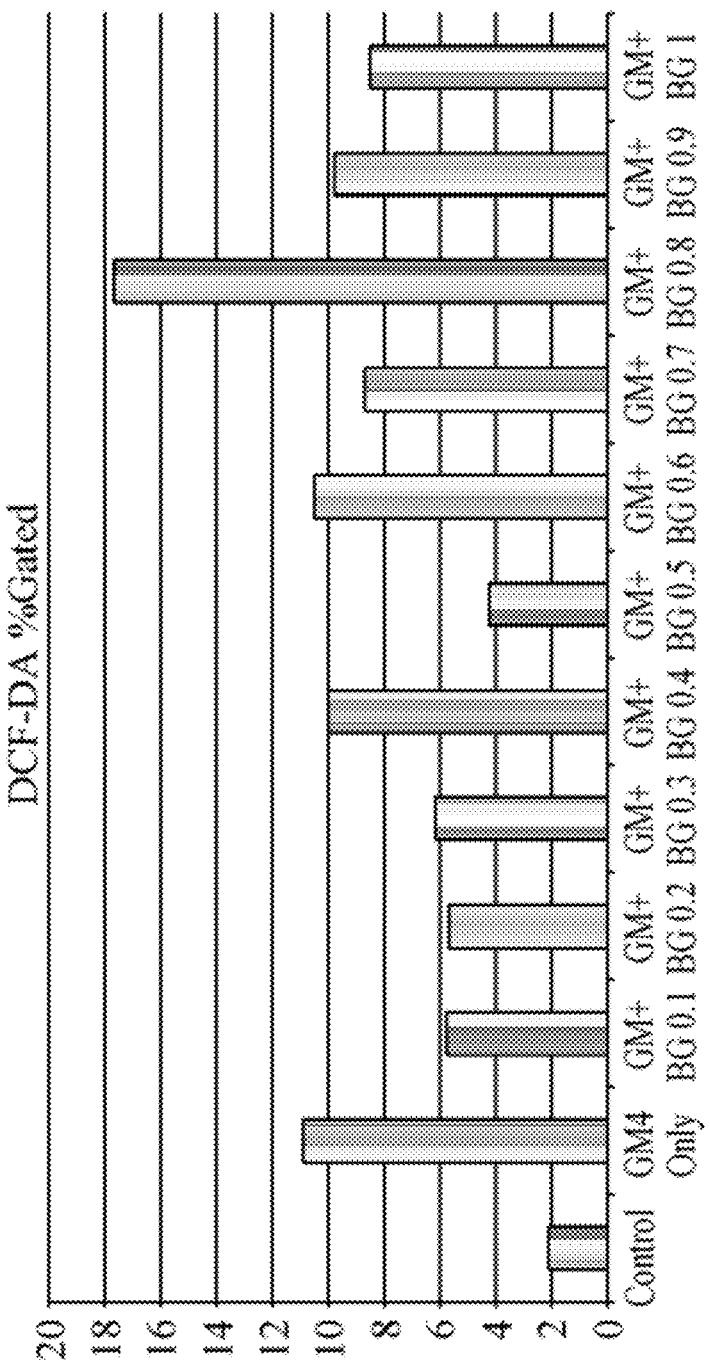

As seen from FIGS. 6A and 6B, it was not verified that when the β-glucan was administered, particular protection of hearing loss was shown as compared to the case where only the gentamicin was administered.

EXPERIMENTAL EXAMPLES

Experimental Example 1

Effect of Avenanthramide on Hearing Loss Model In Vitro 1-1. Verification (1) of Hearing Preservation Effect of Administration of Avenanthramide Before Exposure to Noise In order to verify a hearing preservation effect of avenanthramide before exposure to noise, an experiment for measuring a hearing threshold was performed using an auditory brainstem response. A method of measuring the auditory brainstem response (ABR) is a method of evaluating a response to a sound by measuring electric energy when a sound stimulus is transmitted as an electrical signal in the auditory nerve. When the sound reaches the auditory nerve through the outer ear, the middle ear, and the cochlea, the response reflects all states of the outer ear, the middle ear, and the cochlea and reflects the actual sound energy to which the sound energy reaches the brain. The hearing threshold refers to a minimum sensory point of sound that is barely audible, and in a normal mouse, the response is observed even on the small sound having the average of 20 to 30 dB.

Mice to which avenanthramide was administered and untreated control mice were divided into four groups of eight mice, respectively, and evaluated. The noise was exposed with a pure tone of 90 dB of 8 KHz for 6 hours and 10 μg/kg of avenanthramide was intraperitoneally administered to mice before 6 hours and 24 hours of exposure to noise. During the auditory brainstem response test, the stimulus sound was evaluated by lowering the sound gradually from 90 dB by 5 dB with a click sound of a broadband stimulus sound, and the smallest sound of the response was set as the threshold. In addition, the hearing threshold was measured with a stimulus sound of 4 kHz, 8 kHz, 16 kHz, 24 kHz, and 32 kHz tone burst (TB), and in order to verify a hearing preservation effect of avenanthramide, the experiment for measuring the hearing threshold was performed in the same manner as above. The result was illustrated in FIG. 7.

As seen from FIG. 7, it was verified that the treatment with avenanthramide had a lower threshold than that of exposure to noise without avenanthramide treatment. In particular, treatment with avenanthramide before 24 hours of exposure to noise had a similar threshold to a control, and it means no hearing damage (see the graph on the left of FIG. 7). In addition, as a result of measuring the hearing threshold at 4 kHz, 8 kHz, and 16 kHz TB stimuli sound, the effect of preserving the hearing threshold was high in a group administered with avenanthramide, and as a result, it was verified that avenanthramide was effective in preventing noise-induced hearing loss (see the graph on the right of FIG. 7).

1-2. Verification (2) of Hearing Preservation Effect of Administration of Avenanthramide Before Exposure to Noise The noise was exposed with a pure tone of 90 dB 8 KHz for 6 hours and 10 μg/kg of avenanthramide was intraperitoneally administered to mice before 6 hours and 24 hours of exposure to noise. Then, the ABR test was performed after two weeks of noise induction in the same manner as Experimental Example 1-1 and the result was illustrated in FIG. 8.

As seen from FIG. 8, it was verified that the treatment with avenanthramide had a lower threshold of 20 dB or more than that of exposure to noise without avenanthramide treatment (see the graph on the left of FIG. 8). In addition, as a result of measuring the hearing threshold at 4 kHz, 8 kHz, and 16 kHz TB stimuli sound, like the test result when using the click stimulus sound, the effect of preserving the hearing threshold was high in a group administered with avenanthramide, and as a result, it was verified that avenanthramide was effective in preventing noise-induced hearing loss (see the graph on the right of FIG. 8).

1-3. Verification (3) of Hearing Preservation Effect of Administration of Avenanthramide Before Exposure to Noise The noise was exposed with a pure tone of 95 dB 8 KHz for 6 hours and 10 μg/kg of avenanthramide was intraperitoneally administered to mice before 6 hours and 24 hours of exposure to noise. Then, the ABR test was performed after two weeks of noise induction in the same manner as Experimental Example 1-1 and the result was illustrated in FIG. 9.

As seen from FIG. 9, it was verified that the treatment with avenanthramide had a lower threshold of 40 dB or more than that of exposure to noise without avenanthramide treatment. On the other hand, the treatment with avenanthramide showed almost the same threshold value as the control, and thus, it means that no hearing damage was observed (see the graph on the left of FIG. 9). In addition, as a result of measuring the hearing threshold at 4 kHz, 8 kHz, and 16 kHz TB stimuli sound, like the test result when using the click stimulus sound, the effect of preserving the hearing threshold was high in a group administered with avenanthramide, and as a result, it was verified that avenanthramide was effective in preventing noise-induced hearing loss (see the graph on the right of FIG. 9).

Until now, the present invention has been described with reference to the embodiments. It is understood to those skilled in the art that the present invention may be implemented as a modified form without departing from an essential characteristic of the present invention. Therefore, the disclosed embodiments should be considered from not a limitative viewpoint but an explanatory viewpoint. The scope of the present invention is described in not the above description but the appended claims, and it should be interpreted that all differences within the scope equivalent thereto are included in the present invention.

What is claimed is:

1. A method for treating hearing loss of a subject, the method comprising administering to the subject in need thereof a composition comprising avenanthramide as an active ingredient,
    wherein the hearing loss includes hearing loss due to noise or hearing loss due to administration of an ototoxic drug.

2. The method of claim 1, wherein the composition comprises an oat extract including avenanthramide.

3. The method of claim 1, wherein the avenanthramide includes avenanthramide-A, avenanthramide-B, avenanthramide-C, avenanthramide-O, or avenanthramide-P.

4. The method of claim 1, wherein the content of the avenanthramide-C is 0.5 μM or more.

5. The method of claim 1, wherein the ototoxic drug is at least one selected from a group consisting of streptomycin, kanamycin, gentamicin, neomycin, amikacin, tobramycin, netilmicin, dibekacin, sisomycin, livodomycin, cisplatin and carboplatin.

6. The method of claim 1, wherein the composition is a pharmaceutical composition formulated by a tablet, a foam, a granule, or a capsule.

7. The method of claim 1, wherein the composition is a pharmaceutical composition formulated by a tablet, a foam, a granule, or a capsule.

8. The method of claim 1, wherein the subject has a cancer, and the composition further comprises an anticancer agent.

* * * * *